United States Patent [19]

Simons

[11] 4,434,246
[45] Feb. 28, 1984

[54] PROCESS FOR PREPARING ETHYLENE GLYCOL AND LOWER MONOHYDRIC ALCOHOLS FROM SYNGAS USING A NOVEL CATALYST SYSTEM

[75] Inventor: Leslie H. Simons, Austin, Tex.

[73] Assignee: Texaco Inc., White Plains, N.Y.

[21] Appl. No.: 344,259

[22] Filed: Feb. 1, 1982

[51] Int. Cl.³ ............................................. C07C 27/06
[52] U.S. Cl. ................................... 518/700; 518/715; 502/164; 502/150; 502/170
[58] Field of Search ............................... 518/700, 715

[56] References Cited

U.S. PATENT DOCUMENTS

| | | | |
|---|---|---|---|
| 2,636,046 | 4/1953 | Gresham | 518/718 |
| 4,265,828 | 5/1981 | Knifton | 518/700 |
| 4,315,993 | 2/1982 | Knifton | 518/700 |

OTHER PUBLICATIONS

Fonseca et al., High Pressure Science & Technology, Sixth Airapt Conference; Plenum Press, New York, (1979), pp. 733–738.

*Primary Examiner*—Howard T. Mars
*Attorney, Agent, or Firm*—Jack H. Park; Richard A. Morgan; Walter D. Hunter

[57] ABSTRACT

Ethylene glycol and lower monohydric alcohols are prepared from syngas in good yield by contacting a mixture of carbon monoxide and hydrogen with a catalyst system comprising a ruthenium-containing compound and a special substituted aromatic compound both dispersed in a low melting quaternary phosphonium salt and heating the resulting mixture at a temperature of at least 150° C. and a pressure of at least 500 psi for sufficient time to produce the desired ethylene glycol and monohydric alcohols, and then removing the same from the reaction mixture.

18 Claims, No Drawings

PROCESS FOR PREPARING ETHYLENE GLYCOL AND LOWER MONOHYDRIC ALCOHOLS FROM SYNGAS USING A NOVEL CATALYST SYSTEM

BACKGROUND OF THE INVENTION

1. Field of the Invention

This invention relates to a new process for preparing ethylene glycol and lower monohydric alcohols. More particularly, the invention relates to an improved process for preparing ethylene glycol and lower monohydric alcohols from syn gas using a novel catalyst system.

Specifically, the invention provides a new process for preparing ethylene glycol and lower monohydric alcohols from syngas in good yields, which process comprises contacting a mixture of carbon monoxide and hydrogen with a catalyst comprising a ruthenium-containing compound and a special substituted aromatic compound both dispersed in a low melting quaternary phosphonium salt, and heating the resulting mixture at a temperature of at least 150° C. and a pressure of at least 500 psi for sufficient time to produce the desired ethylene glycol and monohydric alcohols.

2. Prior Art

Ethylene glycol is a chemical which has found wide use in industry. It is used, for example, in the preparation of plasticizers for vinyl polymers and as a component in polyester fibers and antifreeze formulations. In view of its many uses, there is a need to find new and more economical methods for preparing the ethylene glycol.

One proposed mode of making ethylene glycol involves the reaction of carbon monoxide with hydrogen in the presence of variously proposed catalyst systems. In general, the mixture of carbon monoxide and hydrogen, commonly known as synthesis gas or syngas, is reacted at elevated temperatures and pressures in the presence of the proposed catalysts. For example, Belgium Pat. No. 793,086 and U.S. Pat. No. 3,940,432, describe the cosynthesis of ethylene glycol and methanol from mixtures of carbon monoxide and hydrogen using a complex rhodium catalyst. U.S. Pat. No. 3,833,634 describes the use of various other metals as catalysts but indicates that only rhodium and cobalt were effective in producing the ethylene glycol.

However, many of these proposed processes are limited by the nature and activity of the catalyst systems. For example, many of the catalyst systems have poor selectivity, have limited solubility and are expensive to prepare.

It is an object of the invention, therefore, to provide an improved method for preparing ethylene glycol and monohydric alcohols. It is a further object to provide a new process for preparing ethylene glycol and monohydric alcohols from syngas using a new catalyst system. It is a further object to provide a new process for preparing ethylene glycol from syngas using an economical catalyst system and one that has good selectivity as to the formation of the desired products. Other objects and advantages of the invention will appear hereinafter.

SUMMARY OF THE INVENTION

It has now been discovered that these and other objects may be accomplished by the process of the invention comprising contacting a mixture of carbon monoxide and hydrogen with a catalyst comprising a ruthenium-containing compound and a special substituted aromatic compound both dispersed in a low melting quaternary phosphonium base or salt, and heating the resulting mixture at a temperature of at least 150° C. and a pressure of at least 500 psi for sufficient time to produce the desired ethylene glycol and monohydric alcohols. It was surprising to find that with the use of these special catalyst systems one can obtain the formation of ethylene glycol and the monohydric alcohols as related catalyst systems produced no ethylene glycol. Further advantage is found in the fact that the new catalyst systems are in general more economical than those used heretofore in this type of reaction and are effective at moderate temperatures and pressures, thus avoiding the use of extreme conditions required in many of the prior known processes.

The process of the invention as far as the formation of the desired ethylene glycol is concerned may be represented by the following equation:

Typical yields of the ethylene glycol based on total liquid products range from 2 to about 16 wt%.

DETAILED DESCRIPTION OF THE INVENTION

In the operation of the process of the invention, ethylene glycol and lower monohydric alcohols, such as methanol and ethanol, are prepared concurrently from a synthesis gas mixture of carbon monoxide and hydrogen by a process comprising the following steps:

(a) Contacting the said mixture of carbon monoxide and hydrogen with a catalyst comprising a ruthenium-containing compound and a special substituted aromatic compound, both dispersed in a low melting quaternary phosphonium base.

(b) Heating the said mixture to a temperature of at least 150° C. and a pressure of at least 500 psi with sufficient carbon monoxide and hydrogen to satisfy the above-noted stoichiometry of the desired ethylene glycol synthesis, until formation of the desired ethylene glycol has been achieved, and, (c) Preferably isolating the said ethylene glycol and monohydric alcohols from the reaction mixture.

In order to present the inventive concept of the present invention in the greatest possible detail, the following supplementary disclosure is submitted. The process of the invention is practiced as follows:

As noted, the new catalyst system used in the process of the invention contains a ruthenium-containing compound and a special substituted aromatic compound. The ruthenium-containing compound to be used may be chosen from a wide variety of organic and inorganic compounds, complexes, etc. It is only necessary that the catalyst component actually employed contain the ruthenium in any of its ionic states.

The ruthenium-containing compound employed may take many different forms. For example, the ruthenium may be added to the reaction mixture in an oxide form, as in the case of, for example, ruthenium(IV) oxide hydrate, anhydrous ruthenium(IV) dioxide and ruthenium(VIII) tetroxide. Alternatively, it may be added as the salt of a mineral acid, as in the case of ruthenium(III) chloride hydrate, ruthenium(III) bromide, ruthenium(III) triiodide, tricarbonyl ruthenium nitrate, or as the salt of a suitable organic carboxylic acid, such as for example, ruthenium(III) acetate, ruthenium naphthenate, ruthenium valerate and ruthenium complexes with carbonyl-containing ligands such as ruthenium(III) acetylacetonate. The ruthenium may also be added to the reaction mixture as a carbonyl or hydrocarbonyl derivative. Suitable examples include triruthenium dodecacarbonyl and other hydrocarbonyls such as $H_2Ru_4(CO)_{13}$ and $H_4Ru_4(CO)_{12}$, and substituted carbonyl species such as the tricarbonyl ruthenium(II) chloride dimer, $(Ru(CO)_3Cl_2)_2$.

Preferred ruthenium-containing compounds include oxides of ruthenium, ruthenium salts of organic carboxylic acids and ruthenium carbonyl or hydrocarbonyl derivatives. Particularly preferred are the following members: ruthenium(IV) dioxide hydrate, ruthenium(VIII) tetraoxide, anhydrous ruthenium(IV) oxide, ruthenium acetate, ruthenium(III) acetylacetonate, and triruthenium dodecacarbonyl.

The special substituted aromatic compound to be used in the catalyst composition comprise those organic compounds having at least one aromatic ring substituted with at least one dissimilar substituent which imparts different chemical properties. Such substituents include the aliphatic or cycloaliphatic hydrocarbon radicals, halogen atoms, and the like. The aromatic base may be mononuclear or polynuclear and may be fused rings or rings separated by suitable substituents, such as aliphatic hydrocarbons. Illustrative examples include, among others, the arene compounds, such as ethylbenzene, triethylbenzene, butylbenzene, tributyl benzene, triamylbenzene, hexamethylbenzene, allylbenzene, triallylbenzene, cyclohexylbenzene, p-xylene, m-xylene, p-xylene, styrene, trans-stilbene, triphenylethylene, tetraphenylethylene, phenylacetylene, diphenylacetylene, diphenylmethane, triphenylmethane, durene, isodurene, 1,3,5-trimethylbenzene, 1,2,4-trimethylbenzene, and the like, and mixtures thereof. Other examples include the halogenated aromatic compounds, such as monochlorobenzene, dichlorobenzene, hexachlorobenzene, monobromobenzene, monoiodobenzene, dichloronaphthalene, dichlorodurene, dichlorocyclohexylbenzene, dichlorophenylacetylene, chlorostyrene, dichlorostilbene, tetrachlorodiphenylmethane, and the like.

Preferred aromatic compounds to be used include the arene compounds which have at least one and preferably 1 to 6 aliphatic or cycloaliphatic radicals attached to a single aromatic ring. Coming under special consideration are the benzene compounds substituted with from 1 to 6 alkyl or cycloalkyl radicals, preferably containing from 1 to 8 carbon atoms each, such as for example, methylbenzene, trimethylbenzene, tributylbenzene, cyclohexylbenzene, trioctylbenzene, hexamethylbenzene, hexabutylbenzene, and the like, and mixtures thereof.

Coming under special consideration, particularly because of the good selectivity obtained therefrom, are the substituted aromatic compounds of the formula

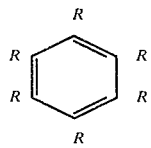

wherein R is an alkyl, alkenyl, cycloalkyl or cycloalkenyl, radical, or halogen atom.

The ruthenium-containing compound and the substituted aromatic compound are preferably first dispersed in a low melting quaternary phosphonium salt. The quaternary phosphonium base or salt selected must be relatively low melting, i.e. have a melting point below the temperature of the reaction mixture. Usually quaternary phosphonium compounds employed have a melting point less than about 180° C. and preferably a melting point less than 150° C.

Suitable quaternary phosphonium salts have the formula

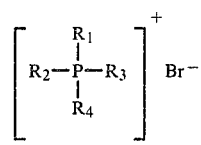

wherein $R_1$, $R_2$, $R_3$, and $R_4$ are alkyl radicals, radicals bonded to the phosphorous atom. The alkyl radicals useful in this instance include those alkyl radicals having 1 to 20 carbon atoms in a branched or linear alkyl chain, such as methyl, ethyl, n-butyl, iso-butyl, octyl, 2-ethylhexyl and dodecyl radicals. Tetraethylphosphonium bromide and tetrabutylphosphonium bromide are typical examples presently in commercial production.

Illustrative examples of suitable quaternary phosphonium salts include tetrabutylphosphonium bromide, tetraoctylphosphonium bromide, tetraamylphosphonium bromide, tetradecylphosphonium bromide, tetrahexadecylphosphonium bromide, tetrapropylphosphonium bromide, tetraisobutylphosphonium bromide and tetraheptyl phosphonium bromide.

The preferred quaternary salts are generally the tetralkylphosphonium bromides containing alkyl groups having 1 to 20 carbon atoms, such as methyl, ethyl, butyl, amyl, hexyl, isobutyl, dodecyl, hexadecyl, and octadecyl. Tetraalkylphosphonium bromides containing 1 to 8 carbon atoms, such as the tetrabutylphosphonium bromide, tetrahexylphosphonium bromide, and tetraoctylphosphonium bromide are the most preferred.

Generally, in the catalyst system used in the process of the invention, the molar ratio of the ruthenium-containing compound to the quaternary phosphonium salt or base will range from about 1:0.01 to about 1:100 or more and, preferably, will be from about 1:5 to about 1:50.

The quantity of ruthenium-containing compound and the substituted aromatic compound to be used in the process of the invention may vary over a wide range. The process is conducted in the presence of a catalytically effective amount of the active ruthenium-containing compound and the active substituted aromatic compound which gives the desired product in a reasonable yield. The reaction proceeds when employing as little as about $1 \times 10^{-6}$ weight percent, and even lesser amounts of the ruthenium-containing compound, together with as little as about $1 \times 10^{-6}$ weight percent of the aromatic compound, or even lesser amounts, based on the total weight of the reaction mixture. The upper concentration is dictated by a variety of factors including catalyst cost, partial pressures of carbon monoxide and hydrogen operating temperatures, etc. A ruthenium-containing compound concentration of from about $1 \times 10^{-5}$ to about 10 weight percent in conjunction with a substituted aromatic compound concentration of from about $1 \times 10^{-5}$ to about 5 percent, based on the total weight of the reaction mixture is generally desirable in the practice of this invention. The preferred ruthenium to aromatic compound mole ratios are from 10:1 to 1:10.

Particularly superior results are obtained when the above-noted three components of the catalyst system are combined as follows on a molar basis: ruthenium-containing compound 0.1 to 4 moles, substituted aromatic compound 0.1 to 15 moles, and the quaternary phosphonium base or salt 10 to 60 moles, and still more preferably when the components are combined in the following ratio: ruthenium-containing compound 1 to 4 moles, substituted aromatic compound 1 to 10 moles and the phosphonium base or salt 20 to 50 moles.

The temperature range which can be employed in the process of the invention may vary over a considerable range depending upon experimental factors, including the choice of catalyst, pressure and other variables. A preferred range of operability is from about 150° C. to about 350° C. when superatmospheric pressures of syngas are employed. A narrower range of about 150° C. to 275° C. represents a particularly preferred temperature range.

The prssure employed may also vary over a considerable range, but in most cases is at least above 500 psig. A preferred operating range varies from about 1000 psig to about 7500 psig, although pressures above 7500 psig also provide useful yields of the desired product. The pressures referred to herein represent the total pressure generated by all the reactants, although they are substantially due to the carbon monoxide and hydrogen fractions.

The relative amounts of carbon monoxide and hydrogen which can be initially present in the syngas mixture are variable, and these amounts may be varied over a wide range. In general, the mole ratio of $CO:H_2$ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixtures may also be used in conjunction with up to 50% by volume of one or more other gases. These other bases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide and hydrogen present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The desired product of the reaction, ethylene glycol, will be formed in significant quantities generally varying from about 2 to about 16 wt%. Also formed will be significant amounts of the lower monohydric alcohols, such as methanol and ethanol. Other derivatives such as acetic acid and ethylene glycol ethers, may also be formed in very minor amounts. The ethylene glycol, monohydric alcohols and other by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analyses, or a combination of these techniques. Analyses have, for the most part, been by parts by weight; all temperatures are in degrees centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the unexpected results obtained by using the new catalyst system comprising the ruthenium-containing compound, the substituted aromatic compound both dispersed in a quaternary phosphonium salt or base.

Ruthenium dioxide hydrate, $RuO_2.H_2O$, (4 mmole) and hexamethylbenzene (4 mmole) were dispersed in solid tetrabutylphosphonium bromide (29 mmole) melting at about 100° C., and the mixture transferred in a glass liner to an 850 ml pressure reactor equipped with heating and agitation means. The reactor was sealed, flushed with $H_2/CO$ (1:1). The mixture was heated to 220° C. with rocking, the pressure was raised to 4800 psi by $CO/H_2$ addition from a large surge tank, and the reactor held at 220° C. for 5 hours. Pressure was maintained during that period at about 4800 psi by incremental addition of $CO/H_2$ from the surge tank.

On cooling, a typical gas sample was taken and the excess gas removed. The reddish brown liquid product (15.9) grams represented a 39% gain in weight.

Analysis of the liquid product by GLC showed the presence of:
15.7% ethylene glycol
44.4% methanol
25.7% ethanol
3.2% acetic acid
1.4% water The ethylene glycol, methanol and ethanol were recovered from the crude liquid product by fractional distillation in vacuo. Distillate fractions typically showed an ethylene glycol content of greater than 10 wt%.

The above results were surprising in view of the results obtained by the use of related catalyst systems in the same process.

For example, the procedure noted above was repeated with the exception that no hexamethyl benzene was added to the catalyst system and the system consisting solely of 4 mmole of the ruthenium dioxide and 29 mmole of the tetrabutylphosphonium bromide. The pressure was maintained at 4400 to 4800 psi. At the end of the 5 hour reaction period no ethylene glycol was detected in the reaction mixture.

In addition, the procedure of Example I above was repeated with the exception that the catalyst consisted of 4 mmole of the ruthenium dioxide, 4 mmole of the hexamethyl benzene and 29 mmole of tetrabutylammonium bromide. The temperature was maintained at 220° C. and the pressure at 4800 psi. At the end of the 5 hour reaction period, no ethylene glycol was detected in the reaction mixture.

EXAMPLE II

Example I was repeated with the exception that only 1 mmole of the hexamethyl benzene was employed and the pressure maintained at 4750 to 4800 psi. Related results are obtained.

EXAMPLE III

Example I was repeated with the exception that three mmoles of the hexamethyl benzene was employed with the temperature at 220° C. and the pressure at 4800 psi. Related results are obtained.

EXAMPLE IV

Example I was repeated with the exception that the substituted aromatic compound employed was 2 mmole of 1,3,5-trimethylbenzene. Temperature employed was 220° C. and the pressure of 4750 to 4900 psi. Related results are obtained.

EXAMPLE V

Example I was repeated with the exception that the substituted aromatic compound employed was 2 mmole of chlorobenzene. Temperature employed was 220° C. and pressure of 4750–4825 psi. Related results are obtained.

EXAMPLE VI

Example I was repeated with the exception that the catalyst contained 3 mmole of 1,3,5-trimethylbenzene as the substituted aromatic compound. Temperature employed was 220° C. and pressure of 4800 to 4900 psi. Related results are obtained.

EXAMPLE VII

Example I is repeated with the exception that the ruthenium oxide is replaced with each of the following: $Ru_3(CO)_{12}$, ruthenium acetate, ruthenium benzoate. Related results are obtained.

EXAMPLE VIII

Example I is repeated with the exception that the substituted aromatic compound is replaced with each of the following: allyl benzene, durene, and dichlorobenzene. Related results are obtained.

What is claimed is:

1. A process for preparing ethylene glycol and lower monohydric alcohols from syngas which comprises contacting a mixture of carbon monoxide and hydrogen with a catalyst system comprising a ruthenium-containing compound and a substituted aromatic hydrocarbon compound wherein the substituted aromatic hydrocarbon compound is a member of the group consisting of (1) mononuclear and polynuclear aromatic hydrocarbon compounds substituted on at least one ring carbon atom with an alkyl, alkenyl, cycloalkenyl or cycloalkyl group, and (2) mononuclear and polynuclear aromatic hydrocarbon compounds substituted on at least one ring carbon atom with a halogen atom, the ruthenium-containing compound and the substituted aromatic hydrocarbon compound being dispersed in a low melting quaternary phosphonium bromide, wherein the ruthenium-containing compound, substituted aromatic hydrocarbon and quaternary phosphonium salt are utilized in a mole ratio of ruthenium containing compound 1 to 4 moles, substituted aromatic hydrocarbon 1 to 10 moles and the phosphonium salt 20 to 50 moles, and heating the resulting mixture at a temperature of 150° C. to 350° C. and a pressure of 500 psi to 5500 psi for sufficient time to produce the desired ethylene glycol and monohydric alcohols.

2. A process as in claim 1 wherein the ruthenium-containing compound is selected from the group consisting of one or more oxides of ruthenium, ruthenium complexes of carbonyl-containing ligands, ruthenium salts of organic acids and ruthenium-carbonyl and hydrocarbonyl compounds.

3. A process as in claim 1 wherein the ruthenium-containing compound is selected from the group consisting of anhydrous ruthenium(IV) dioxide, ruthenium(IV) dioxide hydrate, ruthenium(VIII) tetraoxide, ruthenium acetate, ruthenium propionate, ruthenium(III) acetylacetonate and triruthenium dodecarbonyl.

4. A process as in claim 1 wherein the substituted aromatic hydrocarbon compound is a compound of the formula $$\begin{array}{c} R \\ R-\underset{R}{\underset{|}{\bigcirc}}-R \\ R \quad R \end{array}$$

wherein R is a member of the group consisting of alkyl, alkenyl, cycloalkyl, cycloalkenyl radicals and halogen atoms.

5. A process as in claim 1 wherein the substituted aromatic hydrocarbon compound is an alkyl-substituted aromatic hydrocarbon.

6. A process as in claim 1 wherein the substituted aromatic hydrocarbon compound is a polyalkyl substituted benzene.

7. A process as in claim 1 wherein the substituted aromatic hydrocarbon compound is hexamethyl benzene.

8. A process as in claim 1 wherein the ruthenium-containing compound is a ruthenium oxide and the substituted aromatic hydrocarbon compound is an alkyl-substituted aromatic hydrocarbon.

9. A process as in claim 1 wherein the quaternary phosphonium bromide has a melting point less than about 150° C.

10. A process as in claim 1 wherein the quaternary phosphonium bromide is a tetraalkyl phosphonium bromide.

11. A process as in claim 1 wherein the quaternary phosphonium bromide is a tetralkyl phosphonium halide wherein the alkyl groups contain from 1 to 6 carbon atoms each.

12. A process as in claim 1 wherein the quaternary phosphonium bromide is tetrabutyl phosphonium bromide.

13. A process as in claim 1 wherein the carbon monoxide and hydrogen are utilized in a mole ratio varying from 5:1 to 1:5.

14. A process for preparing ethylene glycol and lower monohydric alcohols from syngas which comprises contacting a mixture of carbon monoxide and hydrogen in a mole ratio of 1:5 to 5:1 with a catalytic amount of a catalyst system comprising a ruthenium oxide and a substituted aromatic compound having a plurality of alkyl groups attached to an aromatic hydrocarbon ring, the said ruthenium-containing compound and substituted aromatic compound being dispersed in a tetralkyl phosphonium bromide melting below 150° C. and heating the resulting mixture at a temperature of 150° C. to 350° C. and a pressure of 1000 psi to 5500 psi for sufficient time to form the desired ethylene glycol and monohydric alcohol, and then recovering the same from the reaction mixture.

15. A process as in claim 14 wherein the aromatic compound is hexamethyl benzene.

16. A process as in claim 14 wherein the aromatic compound is 1,3,5-trimethylbenzene.

17. A process as in claim 14 wherein the aromatic compound is a halogen-substituted benzene.

18. A process as in claim 1 and 14 wherein the ruthenium-containing compound is ruthenium dioxide hydrate.

* * * * *